United States Patent
Tsuchihashi et al.

(10) Patent No.: US 7,363,801 B2
(45) Date of Patent: Apr. 29, 2008

(54) GAS CHROMATOGRAPH SAMPLE INJECTOR

(75) Inventors: Hitoshi Tsuchihashi, Osaka (JP); Akihiro Miki, Kyoto (JP); Munehiro Katagi, Osaka (JP); Mayumi Nishikawa, Osaka (JP); Kei Zaitsu, Nara (JP)

(73) Assignee: Shimadzu Corporation, Kyoto (JP)

( * ) Notice: Subject to any disclaimer, the term of this patent is extended or adjusted under 35 U.S.C. 154(b) by 314 days.

(21) Appl. No.: 11/311,263

(22) Filed: Dec. 20, 2005

(65) Prior Publication Data

US 2007/0084302 A1 Apr. 19, 2007

(30) Foreign Application Priority Data

Oct. 14, 2005 (JP) ............................. 2005-299479

(51) Int. Cl.
*G01N 30/02* (2006.01)
(52) U.S. Cl. ........................................ 73/23.41; 422/89
(58) Field of Classification Search ............... 73/23.41
See application file for complete search history.

(56) References Cited

U.S. PATENT DOCUMENTS 5,242,471 A * 9/1993 Markham et al. ............... 95/87
5,281,397 A * 1/1994 Ligon et al. ................... 422/89

FOREIGN PATENT DOCUMENTS

JP 2001-337078 12/2001

* cited by examiner

*Primary Examiner*—Robert Raevis
(74) *Attorney, Agent, or Firm*—Westerman, Hattori, Daniels & Adrian, LLP.

(57) ABSTRACT

In a sample injector for a gas chromatograph, the present invention improves the throughput of a GC analysis including the derivation of a target compound and reduces the tedious work of handling a reagent for the derivation. According to the present invention, a derivation reagent R is suctioned into a microsyringe 10, after which a small amount of air and a sample P to be analyzed are successively suctioned so that the reagent, the air and the sample are held in this order, from top to bottom. Then, the needle 11 of the microsyringe 10 is inserted through the septum 3 into the sample-vaporizing chamber 2, and the plunger 12 is pushed halfway through so that only the sample is injected into the sample-vaporizing chamber 2. The sample thus injected is quickly vaporized into a gas sample and introduced into the column 6, where the target compound contained in the gas sample adheres to the inner wall of an inlet section of the column 6. When several seconds have passed after the injection of the sample, the plunger 12 is further pushed down to inject the reagent into the sample-vaporizing chamber 2. Then, the reagent is turned into gas and introduced into the column 6, where the reagent reacts with the compound to produce a derivative. Subsequently, the temperature of the column 6 is raised to carry out a GC analysis.

6 Claims, 4 Drawing Sheets

GAS CHROMATOGRAPH SAMPLE INJECTOR

The present invention relates to a sample injector for injecting a sample into a sample-vaporizing chamber located at the inlet of a column of a gas chromatograph. More specifically, it relates to a sample injector for a gas chromatograph used for analyzing a sample that has to be, or should be preferably, converted into a derivative.

BACKGROUND OF THE INVENTION

In an analysis using a gas chromatograph, the compound to be analyzed is sometimes converted into a derivative that is easier to analyze or detectable with higher sensitivity, if the compound as is cannot be detected at all or is detectable only with low sensitivity and accuracy. Conversion of a compound into a derivative uses a reagent that causes various kinds of chemical reactions with a functional group of the compound to be analyzed. Examples of the derivation process are silylation, alkyl-esterification, acrylation and dimethylsilylation.

Derivation of a sample containing a target compound generally includes the following steps: initially, a dry nitrogen gas is sprayed onto a liquid sample as is, or after being concentrated, to vaporize the sample and dry it on the inner wall of a container, such as a test tube or a vial; a predetermined derivation reagent solution is put into the container and mix it with the sample; and the mixture is left at rest for some time to obtain a derivative of the target compound contained in the sample.

Such a manual derivation process consumes time and labor because it requires the liquid sample to be once vaporized and dried. Accordingly, the throughput of the gas chromatograph analysis deteriorates if the derivation process is performed; it will take a very long time if there are a large number of specimens to be analyzed. Also, even if there are only a small number of specimens, the time-consuming method is hardly available in some special cases, such as a test for illegal drugs where the test result should be quickly obtained. Thus, to enhance the throughput of a gas chromatograph analysis including a derivation process still remains a big challenge.

Also, the conventional method is accompanied by the troublesome work of preparing tools for spraying the dry nitrogen gas, for mixing the sample and the derivation reagent, and for other operations performed for the derivation process. Moreover, many reagents require careful handling: some are harmful to humans (i.e. poisonous or deleterious), and some are highly flammable. This requirement limits the scope of people available for this job. It also demands adequate attention to the ventilation and other working conditions. For such reasons, the derivation technique is not actively used in the gas chromatograph analysis except in the case where the derivation is indispensable.

Some conventional apparatuses are provided with an automatic mechanism intended to eliminate troublesome manual work for the derivation process. For example, the Japanese Unexamined Patent Publication No. 2001-337078 discloses a gas chromatograph having an automatic pre-treating function for automatically performing a pre-treatment including the derivation process. However, this conventional apparatus requires plural thermostatic chambers, a channel selector valve and other devices, which inevitably makes the apparatus large and complex. Therefore, its production cost is higher than that of ordinary gas chromatographs.

To solve the above-described problems, the present invention provides a simple and inexpensive sample injector for a gas chromatograph, which is capable of improving the throughput of the analysis by reducing the time and labor for the derivation process.

SUMMARY OF THE INVENTION

Thus, the first mode of the present invention provides a sample injector for injecting a liquid sample into a sample-vaporizing chamber located at the inlet of a column of a gas chromatograph, which is used to analyze a sample that needs to undergo a derivation process before an analysis, and the sample injector includes:

a) a liquid-holding device having a syringe with a needle attached to its tip and a plunger slidably inserted into the syringe;

b) an actuator for activating the plunger; and c) a controller for controlling the actuator to push or pull the plunger so that:

a derivation reagent is suctioned into the syringe, whereafter a sample to be analyzed is suctioned so that the sample is held closer to the needle and the derivation reagent farther from the needle;

the needle is inserted into the sample-vaporizing chamber; and the plunger is pushed into the syringe in a manner so that the sample held in the syringe is first injected into the sample-vaporizing chamber, and then the derivation reagent held in the syringe is injected into the sample-vaporizing chamber when a predetermined period of time has elapsed after the injection of the sample into the sample-vaporizing chamber.

In the sample injector according to the first mode of the present invention, the actuator, which is controlled by the controller, pulls the plunger while the tip of the needle is immersed in the derivation reagent, whereby a predetermined quantity of the derivation reagent is suctioned into the syringe. Subsequently, the tip of the needle is immersed in the sample, and the actuator further pulls the plunger to suction the sample into the syringe. It is preferable to suction a small quantity of air between the derivation reagent and the sample so as to form an air layer between the derivation reagent and the sample within the syringe. This prevents the derivation reagent from being accidentally mixed with the sample.

With the derivation reagent and the sample thus held within the syringe, the needle is inserted into the sample-vaporizing chamber, and the plunger is pushed so that only the sample located closer to the needle within the syringe is injected into the sample-vaporizing chamber. After the entire sample is injected, the plunger is temporarily stopped. The injected sample is vaporized within the sample-vaporizing chamber and conveyed into the column by the carrier gas. When a predetermined period of time has elapsed after the injection of the sample, the plunger is further pushed to inject the derivation reagent remaining in the syringe into the sample-vaporizing chamber. The derivation reagent thus injected is also vaporized within the sample-vaporizing chamber and transferred into the column, as in the case of the sample.

When the vaporized sample enters the column, the target component contained in the sample adheres to the inner wall of the column due to the absorption by the wall, whereas the solvent contained in the sample is conveyed away. The aforementioned period of time is preset long enough for the sample injected into the sample-vaporizing chamber to be vaporized, introduced into the column and absorbed at the inlet of the column. This setting enables the target compound to form a thin, dry film covering the inner wall of the column over an area close to the inlet when the predetermined period of time has elapsed after the injection of the sample. After this state has been reached, the vaporized derivation reagent flows into the column and comes in contact with the compound over a wide area, thereby efficiently converting the compound into a derivative. This derivation process takes place at an inlet section of the column, as opposed to conventional cases where the same process was carried out in a test tube, vial or similar container. Subsequently, a temperature-programmed analysis or a similar analysis is carried out, in which the derivative of the compound is vaporized and conveyed through the column for the gas chromatograph analysis.

If the time interval between the injection of the sample into the sample-vaporizing chamber and that of the derivation reagent, or the aforementioned period of time, is allowed to be long enough, it is possible to separately suction and inject the sample and the derivation reagent individually, instead of suctioning both the derivation reagent and the sample into the syringe in advance of the injection.

Accordingly, the second mode of the present invention provides a sample injector for injecting a liquid sample into a sample-vaporizing chamber located at the inlet of a column of a gas chromatograph, which is used to analyze a sample that needs to undergo a derivation process before an analysis, and the sample injector includes:

a) a liquid-holding device having a syringe with a needle attached to its tip and a plunger slidably inserted into the syringe;

b) an actuator for activating the plunger; and c) a controller for controlling the actuator to push or pull the plunger so that:

a sample to be analyzed is suctioned into the syringe;

the needle is inserted into the sample-vaporizing chamber, whereafter the sample held in the syringe is injected into the sample-vaporizing chamber;

the needle is pulled out from the sample-vaporizing chamber, whereafter a derivation reagent is suctioned into the syringe; and the needle is again inserted into the sample-vaporizing chamber, whereafter the derivation reagent held in the syringe is injected into the sample-vaporization chamber when a predetermined period of time has elapsed after the injection of the sample.

It is also possible to separately inject the sample and the derivation reagent from different syringes at different times.

Accordingly, the third mode of the present invention provides a sample injector for injecting a liquid sample into a sample-vaporizing chamber located at the inlet of a column of a gas chromatograph, which is used to analyze a sample that needs to undergo a derivation process before an analysis, and the sample injector includes:

a) a first liquid-holding device having a syringe with a needle attached to its tip and a plunger slidably inserted into the syringe;

b) a second liquid-holding device whose construction is identical to that of the first liquid-holding device;

c) an actuator for separately activating the plunger of each of the first and second liquid-holding devices; and d) a controller for controlling the actuator to push or pull the plungers of the first and second liquid-holding devices so that:

a sample to be analyzed is suctioned into the syringe of the first liquid-holding device;

a derivation reagent is suctioned into the syringe of the second liquid-holding device;

the needle of the first liquid-holding device is inserted into the sample-vaporizing chamber, whereafter the sample held in the syringe of the first liquid-holding device is injected into the same chamber; and the needle of the second liquid-holding device is inserted into the sample-vaporizing chamber, whereafter the derivation reagent held in the syringe of the second liquid-holding device is injected into the sample-vaporizing chamber when a predetermined period of time has elapsed after the injection of the sample into the sample-vaporizing chamber.

In the gas chromatograph sample injectors according to the first through third modes of the present invention, the derivation of the target compound takes place within the column. This eliminates the troublesome work of manually performing the derivation process on the sample to be injected into the sample-vaporizing chamber, thereby significantly improving the efficiency and throughput of the analysis. The sample injector according to the first mode of the present invention can yield a particularly high level of throughput because it allows the time interval between the injection of the sample into the sample-vaporizing chamber and that of the derivation reagent to be minimized as far as the derivation process effectively works.

The gas chromatograph sample injectors according to the first through third modes of the present invention also make it unnecessary to prepare special devices and tools for the derivation; all the operator has to do is to prepare a derivation reagent. Thus, the analysis work is further simplified. Furthermore, since there is no need to manually measure and sample the derivation reagent, the operator can avoid health hazards even if the reagent is harmful to humans and also ensure a high level of safety even if the reagent is flammable. With respect to the hardware construction, the sample injector according to the present invention is almost identical to conventional ones; it does not require any additional hardware components for the derivation process. Therefore, it can be constructed as small as conventional ones with a minimal increase in the production cost.

DETAILED DESCRIPTION OF A PREFERRED EMBODIMENT

Figure 1:
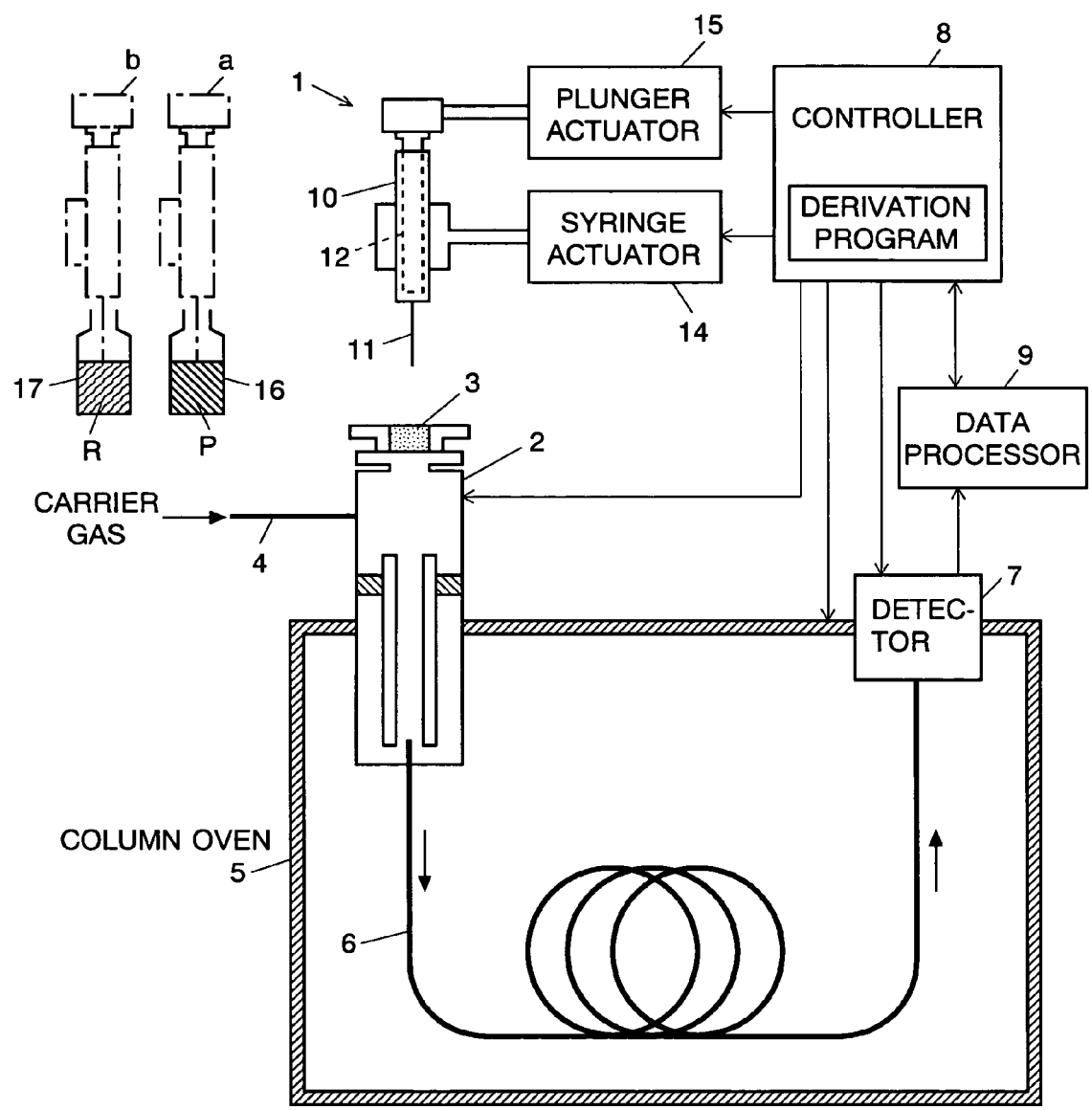
FIG. 1 is a schematic diagram of a gas chromatograph including an embodiment of the sample injector according to the present invention.

An embodiment of the gas chromatograph sample injector according to the present invention is described with reference to the attached drawings. FIG. 1 is a schematic diagram showing an embodiment of a gas chromatograph including a sample injector according to the present invention.

In FIG. 1, the sample injector 1 includes the following elements: a microsyringe 10 having a needle 11 attached to its lower end and a plunger 12 slidably inserted into it; a plunger actuator 15 for pushing or pulling the plunger 12 of the microsyringe 10; and a syringe actuator 14 for vertically moving and horizontally transferring the entire microsyringe 10 within a predetermined range. A sample vial 16 containing a sample P to be analyzed and a reagent vial 17 containing a specified derivation reagent R are located at predetermined positions within the movable horizontal range of the microsyringe 10 transferred by the syringe actuator 14. Alternatively, it is possible to use a transfer mechanism in which the microsyringe 10 suctions a liquid material at a fixed horizontal position and the sample vial 16 and the reagent vial 17 are selectively transferred to that position.

Enclosed in the temperature-controllable column oven 5 is a capillary column 6, at the inlet of which a sample-vaporizing chamber 2 is located. A carrier gas supply pipe 4 for introducing a carrier gas, such as helium gas, into the sample-vaporizing chamber 2 is connected to the chamber 2. The carrier gas supply pipe 4 is fed with a carrier gas at a constant flow rate controlled by a massflow controller (not shown). The carrier gas is introduced through the sample-vaporizing gas into the capillary column 6. The sample-vaporizing chamber 2 used in this embodiment is a split-less type, which may be replaced with a split type.

Located at the exit of the capillary column 6 is a detector 7 for detecting various kinds of components separated by the column 6. Examples of the detector 7 include flame ionization detectors, thermal conductivity detectors, flame photometric detectors, electron capture detectors and flame thermionic detectors. A mass spectrometer is also available as the detector 7. For an analysis that requires high levels of sensitivity and accuracy, it is preferable to use a gas chromatograph/mass spectrometer (GC/MS) as the detector 7.

The electrical circuit includes a controller 8 for controlling the temperatures of the sample-vaporization chamber 2 and the column oven 5, for driving the syringe actuator 14 and the plunger actuator 15, and for performing other operations necessary for GC analysis. It also includes a data processor 9 for processing detection signals generated by the detector 7. The functions of the controller 8 and the data processor 9 may be partially or entirely embodied using a personal computer.

Each of the syringe actuator 14 and the plunger actuator 15 has a source of actuating force, such as a motor. The controller 8 controls the amount of motion of each motor so that the microsyringe 10 and the plunger 12 are actuated (e.g. transferred, pulled or pushed) as described later. For example, if a step motor is used, the controller 8 may perform an open-loop control by sending control pulses to the motor to move the syringe 10 or the plunger 12 by a distance corresponding to the number of the pulses. A closed loop control is also possible, in which the controller 8 monitors the displacement or position of the element concerned while sending a control signal to the motor and regulates the control signal so that the monitored value is maintained as predetermined.

Figure 2:
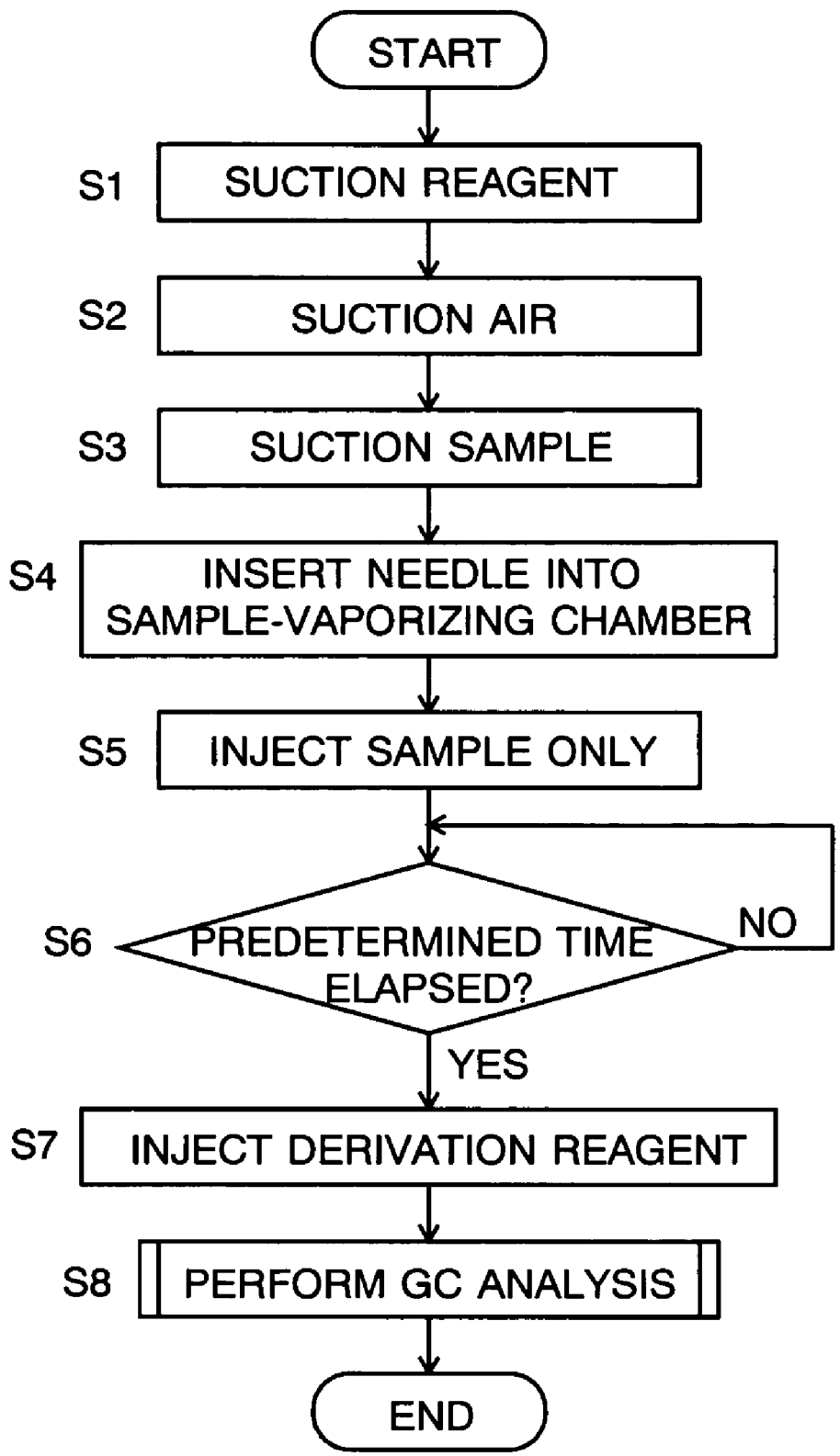
FIG. 2 is a flowchart showing the control steps of the gas chromatograph analysis including a derivation process performed by the gas chromatograph of the present embodiment.

The controller 8 includes a read-only memory (ROM) or other memory device in which various software programs for controlling each element are stored. Particularly, in the present embodiment, the controller 8 has a control program dedicated to the derivation process. Running this program on a central processing unit (CPU) enables the controller 8 to conduct a special sample-injecting operation for the derivation process to be described later. With reference to FIGS. 2 to 4B, a GC analysis including a derivation process performed under the control of the controller 8 is described below. FIG. 2 is a flowchart showing the control steps of the GC analysis including the derivation process, FIGS. 3A through 3D are illustrations showing a change in the internal state of the microsyringe, and FIGS. 4A and 4B are conceptual diagrams showing how the derivation process takes place within the capillary column.

Figure 3A:
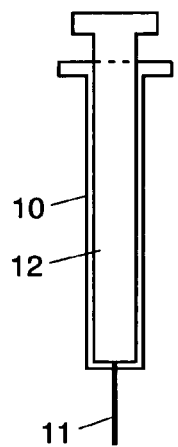
FIGS. 3A to 3D are illustrations showing a change in the internal state of the microsyringe used in the gas chromatograph of the present embodiment.
Figure 3B:
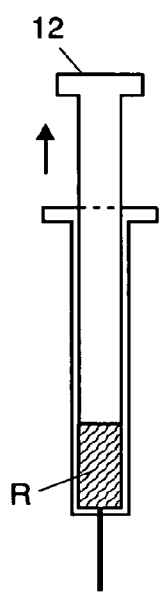
Figure 4A:
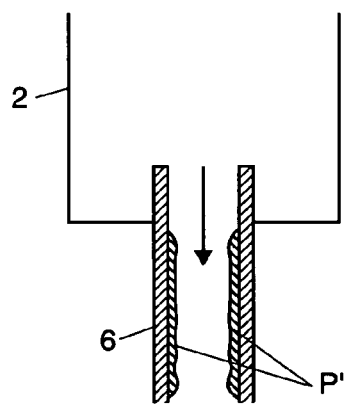
FIGS. 4A and 4B are conceptual diagrams showing how the derivation of a compound takes place.
Figure 4B:
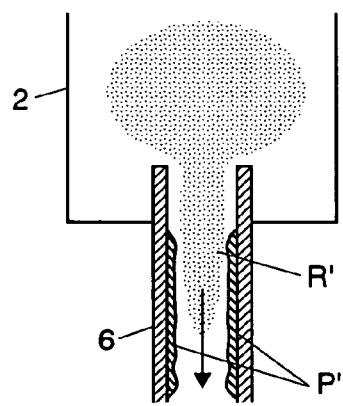

FIG. 3A shows the state where the plunger 12 is fully inserted into the microsyringe 10. This state is hereby regarded as the initial state. Starting from this state, the controller 8 controls the syringe actuator 14 to transfer the microsyringe 10 to a position over the reagent vial 17 and then lower it until the tip of the needle 11 is immersed in the derivation reagent R stored in the reagent vial 17, down to the position indicated by the chain line "b" in FIG. 1. Then, the controller 8 controls the plunger actuator 15 to pull the plunger 12 by a predetermined length so that the derivation reagent R is suctioned into the microsyringe 10 by a predetermined amount (Step S1). As a result, the derivation reagent R is held in the microsyringe 10 as shown in FIG. 3B.

Figure 3C:
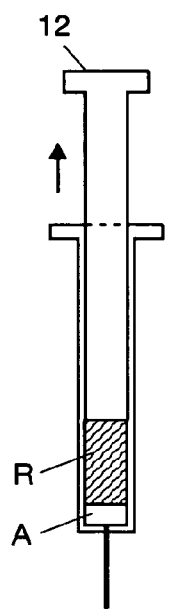

Subsequently, the controller 8 controls the syringe actuator 14 to raise the microsyringe 10 up to a level where the tip of the needle 11 is pulled out from the sample vial 17. Then, it controls the plunger actuator 15 to slightly pull the plunger 12 to suction air into the microsyringe 10 (Step S2). Since the inner diameter of the microsyringe 10 is small, the derivation reagent R suctioned earlier is retained by surface tension from below, under which the suctioned air forms a layer "A", as shown in FIG. 3C.

Figure 3D:
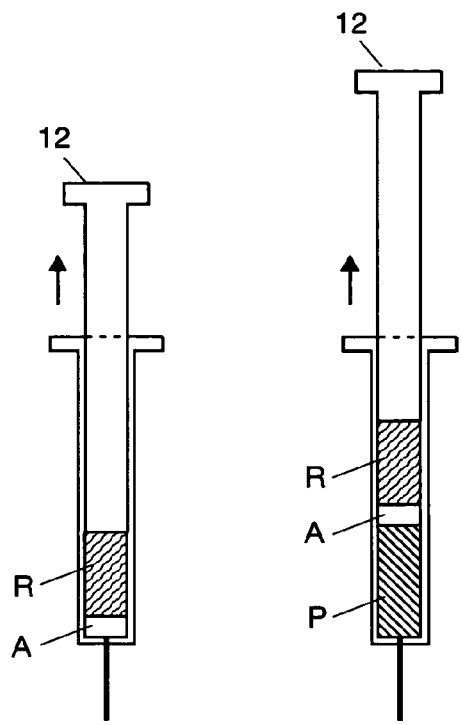

Next, the controller 8 controls the syringe actuator 14 to transfer the microsyringe 10 to a position over the sample vial 16 and then lower it until the tip of the needle 11 is immersed in the sample P contained in the sample vial 16, down to the position indicated by the chain line "a" in FIG. 1. Then, the controller 8 controls the plunger actuator 15 to pull the plunger 12 by a predetermined length so that the sample P is suctioned into the microsyringe 10 by a predetermined amount (Step S3). During this process, the derivation reagent R suctioned first is further pulled up because, as explained earlier, the inner diameter of the microsyringe 10 is small. As a result, the derivation reagent R remains over the air layer "A", under which the sample P forms a layer located closer to the needle 11, as shown in FIG. 3D.

In general, the air layer "A" is not always necessary because the sample P and the derivation reagent R will not quickly mix together when they meet each other. However, the provision of the air layer "A" between the sample P and the derivation reagent R is preferable because:
  It prevents the sample P and the derivation reagent R from diffusing at their interface, which would occur if it were not for the air layer.
  It facilitates the sample-injecting process to be described later, in which the microsyringe 10 should discharge the sample P into the sample-vaporizing chamber 2 while maintaining the derivation reagent R.

With the sample P and the derivation reagent R ready within the microsyringe 10, the controller 8 controls the syringe actuator 14 to transfer the microsyringe 10 to a position over the sample-vaporizing chamber 2 and lower it so that the tip of the needle 11 penetrates through the septum 3 at the top of the sample-vaporizing chamber 2 and reaches the inner space of the sample-vaporizing chamber 2 (Step S4). Then, the plunger actuator 15 is controlled to push down the plunger 12 by a predetermined length, whereby only the sample P, held at the bottom of the microsyringe 10, is injected through the needle 11 into the sample-vaporizing chamber 2 (Step S5).

The sample-vaporizing chamber 2 is heated up to an appropriate temperature (e.g. 250 degrees Celsius) by a heater (not shown). The heat quickly vaporizes the injected sample P into gas, which is then transferred into the capillary column 6 by the carrier gas. The column oven 5, and accordingly the capillary column 6, is maintained at a temperature lower than that of the sample-vaporizing chamber 2, e.g. at about 120 degrees Celsius. This temperature is predetermined lower than the vaporizing temperature of the target compound contained in the sample P. Therefore, upon introduction into the capillary column 6, the target compound contained in the gas sample is absorbed by and held on the inner wall of an inlet section of the column 6. Meanwhile, the solvent is thrust away through the capillary column 6 by the carrier gas.

As a result, as shown in FIG. 4A, the target compound contained in the sample P forms a layer P' on the inner wall of the inlet section of the capillary column 6. It will take a certain length of time for the entire gas sample produced within the sample-vaporizing chamber 2 to enter the capillary column 6. Furthermore, the compound will require some time to dry on the inner wall of the capillary column 6. Therefore, after the injection of the sample in Step S5, the plunger 12 and the microsyringe 10 are held stationary until a predetermined period of time elapses (Step S6). This period depends on the analysis conditions, such as the capacity of the sample-vaporizing chamber 2; usually, it is within a range from 3 to 7 seconds, e.g. about 4 seconds. The period of time should not be too short. Suppose, for example, in an extreme case where the sample and the derivation reagent are almost simultaneously injected into the sample-vaporizing chamber 2. Then, the reagent gasified as described later will enter the column 6 too early for the target compound contained in the sample to adequately adhere to the inner wall of the capillary column 6. This will prevent necessary chemical reactions from fully taking place and thereby deteriorating the derivation efficiency. In contrast, a period of time longer than the aforementioned range might be allowable in some cases. However, longer periods of time will lead to lower degrees of analysis efficiency (or throughput). Therefore, it should be set as short as possible within the range where no problem will arise with respect to the accuracy or sensitivity of the analysis.

When the predetermined period of time has elapsed after the injection of the sample, the controller 8 commands the plunger actuator 15 to push the plunger 12 down to the lowest position, whereby the derivation reagent R remaining in the microsyringe 10 is injected through the needle 11 into the sample-vaporizing chamber 2 (Step S7). As in the case of the sample P, the derivation reagent R is quickly vaporized into gas and, as shown in FIG. 4B, conveyed into the capillary column 6 by the carrier gas. Since the temperature of the column oven 5 is lower than that of the sample-vaporizing chamber 2, the derivation reagent contained in the reagent gas R' introduced into the capillary column 6 also stays at around the inlet of the capillary column 6, where the layer P' of the target compound is present. Thus, the derivation reagent chemically reacts with the compound to convert it into a derivative.

Thus, in the present embodiment, the derivation process in which the derivation reagent chemically reacts with the target compound takes place at the inlet section of the capillary column 6, as opposed to conventional methods where it was performed in a separate container, such as a test tube or vial. The column oven 5 maintains the capillary column 6 at an appropriate temperature (usually about 120 degrees Celsius), which is predetermined to favor the derivation process. The thin layer P' of the target compound covering a large area on the inner wall of the inlet section of the capillary column 6 provides a large contact area for the flow of the reagent gas, thereby improving the derivation efficiency.

The derivative obtained as described above is easier to analyze with a gas chromatograph than the original compound. Thus, the next step is to perform a regular GC analysis: a temperature-programmed analysis in which the temperature is raised to vaporize each component present on the inner wall of the capillary column 6 one after another, including the aforementioned derivative (Step S8). While passing through the capillary column 6, the components are temporally separated before they reach the exit of the column 6. The detector 7 receives each component from the column 6 one after another and produces a detection signal whose strength corresponds to the concentration of the detected component. This signal is sent to the data processor 9, which carries out a quantitative and/or qualitative analysis whereby, for example, creating a chromatogram from the detection signals received within the lapse of time.

If a mass spectrometer is used as the detector 7, it is possible to carry out the qualitative and/or quantitative analysis with higher accuracy by performing a scanning measurement with the mass spectrometer and creating not only chromatograms (e.g. total ion chromatograms) but also mass spectrums and/or mass chromatograms.

As described thus far, in the gas chromatograph including the sample injector according to the present invention, the target compound is converted into a derivative at the inlet of the capillary column 6. The derivative thus obtained is more suitable for GC analysis than the original compound because, for example, its polarity is weaker than that of the original compound. Therefore, identifying and determining the derivative enables the target compound to be analyzed with higher levels of accuracy and sensitivity. Furthermore, setting an appropriate time difference between the injection of the sample into the sample-vaporizing chamber 2 and that of the derivation reagent enables the derivation process to efficiently proceed, as described earlier, so that the target compound can be detected with higher sensitivity.

In the above-described embodiment, the sample injector used a single microsyringe 10 for simultaneously holding both the sample and the derivation reagent, and it controlled the push/pull operation of the plunger 12 so that the sample and the derivation reagent were separately injected into the sample-vaporizing chamber 2 within an appropriate interval of time. By contrast to this construction, the present invention also accepts different mechanisms for separately injecting the sample and the derivation reagent, as in the following modifications.

In the first modification, the sample injector uses a single microsyringe as follows: suction the sample into the microsyringe; inject the sample into the sample-vaporizing chamber; suction the derivation reagent into the same microsyringe; and inject the derivation reagent into the sample-vaporizing chamber when the predetermined period of time mentioned in Step S6 has elapsed after the injection of the sample. This method requires additional steps for transferring the microsyringe. That is, subsequent to the injection of the sample into the sample-vaporizing chamber, it is necessary to transfer the microsyringe to the position for suctioning the derivation reagent from the reagent vial and then return the microsyringe containing the derivation reagent to the position where the reagent can be injected into the sample-vaporizing chamber. For the aforementioned period of time to be as short as 3 to 7 seconds, the syringe actuator needs to operate very quickly. If the operation inevitably takes more time, then the period of time should be longer.

In the second modification, the sample injector uses two microsyringes: one for the sample and the other for the derivation reagent. The actuators are constructed to selectively inject either the sample or the derivation reagent into the sample-vaporizing chamber from the two microsyringes.

Both the first and second modifications do not require any mechanism for temporarily halting the pushing operation of the plunger, as in the first embodiment, because each liquid (i.e. the sample or the derivation reagent) suctioned into the microsyringe is completely discharged by a single injecting operation.

EXAMPLE

Figure 5:
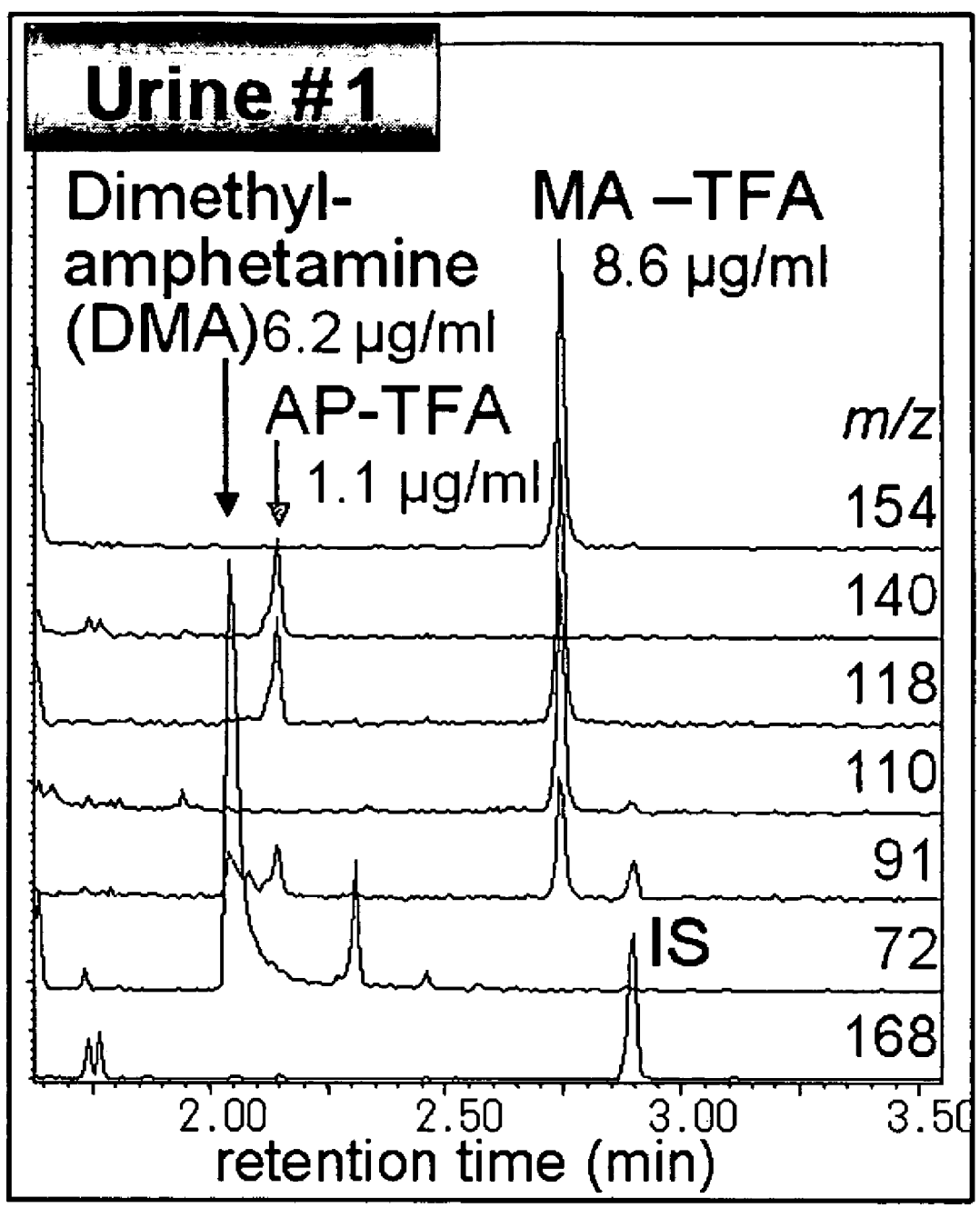
FIG. 5 is a graph showing the result of an analysis test performed using a gas chromatograph/mass spectrometer (GC/MS) including the gas chromatograph of the present embodiment.

A test of the GC analysis was conducted using the gas chromatograph of the above-described embodiment. The target compound was methamphetamine (MA), an illegal drug, and the sample was human urine containing that compound. Methamphetamine as is can be detected only with a very low level of sensitivity by GC analysis. Therefore, it is necessary to convert it into a derivative. In this test, N-Methyl-bis[trifluoroacetamide (MBTFA) was used as the derivation reagent. The test showed that the gas chromatograph constructed as described previously could efficiently produce a derivative in which the active proton contained in the amine base of the methamphetamine was replaced with TFA. FIG. 5 shows a mass chromatogram obtained by analyzing the derivative with a mass spectrometer. Thus, the derivative (MA-TFA) obtained by the derivation process can be detected with high sensitivity, which enables methamphetamine to be identified and determined with high accuracy.

Tests of this kind of compound often need to be quickly done with an adequate level of accuracy. The gas chromatograph using the sample injector according to the present invention is suitable for such an application.

It should be noted that the above-described embodiments and modifications are mere examples of the present invention, which may be further changed or modified within the scope of the present invention.

What is claimed is:

1. A sample injector for injecting a liquid sample into a sample-vaporizing chamber located at an inlet of a column of a gas chromatograph, which is used to analyze a sample that needs to undergo a derivation process before an analysis, the sample injector comprising:
   a) a liquid-holding device having a syringe with a needle attached to its tip and a plunger slidably inserted into the syringe;
   b) an actuator for activating the plunger; and
   c) a controller for controlling the actuator to push or pull the plunger so that:
   a derivation reagent is suctioned into the syringe, whereafter a sample to be analyzed is suctioned so that the sample is held closer to the needle and the derivation reagent farther from the needle;
   the needle is inserted into the sample-vaporizing chamber; and
   the plunger is pushed into the syringe in a manner so that the sample held in the syringe is first injected into the sample-vaporizing chamber, and then the derivation reagent held in the syringe is injected into the sample-vaporizing chamber when a predetermined period of time has elapsed after the injection of the sample into the sample-vaporizing chamber.

2. A sample injector for injecting a liquid sample into a sample-vaporizing chamber located at an inlet of a column of a gas chromatograph, which is used to analyze a sample that needs to undergo a derivation process before an analysis, the sample injector comprising:
   a) a liquid-holding device having a syringe with a needle attached to its tip and a plunger slidably inserted into the syringe;
   b) an actuator for activating the plunger; and
   c) a controller for controlling the actuator to push or pull the plunger so that:
   a sample to be analyzed is suctioned into the syringe;
   the needle is inserted into the sample-vaporizing chamber, whereafter the sample held in the syringe is injected into the sample-vaporizing chamber;
   the needle is pulled out from the sample-vaporizing chamber, whereafter a derivation reagent is suctioned into the syringe; and
   the needle is again inserted into the sample-vaporizing chamber, whereafter the derivation reagent held in the syringe is injected into the sample-vaporization chamber when a predetermined period of time has elapsed after the injection of the sample.

3. A sample injector for injecting a liquid sample into a sample-vaporizing chamber located at an inlet of a column of a gas chromatograph, which is used to analyze a sample that needs to undergo a derivation process before an analysis, the sample injector comprising:
   a) a first liquid-holding device having a syringe with a needle attached to its tip and a plunger slidably inserted into the syringe;
   b) a second liquid-holding device whose construction is identical to that of the first liquid-holding device;
   c) an actuator for separately activating the plunger of each of the first and second liquid-holding devices; and
   d) a controller for controlling the actuator to push or pull the plungers of the first and second liquid-holding devices so that:
   a sample to be analyzed is suctioned into the syringe of the first liquid-holding device;
   a derivation reagent is suctioned into the syringe of the second liquid-holding device;
   the needle of the first liquid-holding device is inserted into the sample-vaporizing chamber, whereafter the sample held in the syringe of the first liquid-holding device is injected into the same chamber; and
   the needle of the second liquid-holding device is inserted into the sample-vaporizing chamber, whereafter the derivation reagent held in the syringe of the second liquid-holding device is injected into the sample-vaporizing chamber when a predetermined period of time has elapsed after the injection of the sample into the sample-vaporizing chamber.

4. The sample injector according to one of claims 1-3, wherein the predetermined period of time is long enough for the sample injected into the sample-vaporizing chamber to be vaporized into gas, introduced into the column and absorbed to an inlet section of the column.

5. The sample injector according to claim 4, wherein the predetermined period of time is within the range from 3 to 7 seconds.

6. The sample injector according to claim 1, wherein the controller commands the actuator to pull the plunger so that a slight amount of air is suctioned into the syringe between the derivation reagent and the sample.

* * * * *